United States Patent
Berthon-Jones

(10) Patent No.: US 7,077,132 B2
(45) Date of Patent: *Jul. 18, 2006

(54) VENTILATORY ASSISTANCE FOR TREATMENT OF CARDIAC FAILURE AND CHEYNE-STOKES BREATHING

(75) Inventor: Michael Berthon-Jones, Leonay (AU)

(73) Assignee: ResMed Limited, New South Wales (AU)

( * ) Notice: Subject to any disclaimer, the term of this patent is extended or adjusted under 35 U.S.C. 154(b) by 0 days.

This patent is subject to a terminal disclaimer.

(21) Appl. No.: 10/865,944

(22) Filed: Jun. 11, 2004

(65) Prior Publication Data

US 2004/0237963 A1 Dec. 2, 2004

Related U.S. Application Data

(63) Continuation of application No. 10/374,487, filed on Feb. 26, 2003, which is a continuation of application No. 09/316,432, filed on May 21, 1999, now Pat. No. 6,532,959.

(30) Foreign Application Priority Data

May 22, 1998 (AU) .................................. PP3663

(51) Int. Cl.
*A61M 16/00* (2006.01)

(52) U.S. Cl. ............................. 128/204.23; 128/204.18

(58) Field of Classification Search ........... 128/200.24, 128/204.18, 204.21, 204.22, 204.23, 204.24, 128/204.26, 204.29, 205.11; 600/529, 532, 600/533, 538
See application file for complete search history.

(56) References Cited

U.S. PATENT DOCUMENTS

| | | | | |
|---|---|---|---|---|
| 4,036,221 A | * | 7/1977 | Hillsman et al. | 128/204.23 |
| 5,107,830 A | | 4/1992 | Younes | |
| 5,353,788 A | * | 10/1994 | Miles | 128/204.23 |
| 5,433,193 A | * | 7/1995 | Sanders et al. | 128/204.18 |

(Continued)

FOREIGN PATENT DOCUMENTS

WO    WO 92/11054    7/1992

(Continued)

*Primary Examiner*—Teena Mitchell
(74) *Attorney, Agent, or Firm*—Gottlieb Rackman & Reisman

(57) ABSTRACT

Method and apparatus for the treatment of cardiac failure, Cheyne Stokes breathing or central sleep apnea are disclosed. A subject is provided with ventilatory support, for example positive pressure ventilatory support using a blower and mask. Respiratory airflow is determined. From the respiratory airflow are derived a measure of instantaneous ventilation (for example half the absolute value of the respiratory airflow) and a measure of longterm average ventilation (for example the instantaneous ventilation low pass filtered with a 100 second time constant). A target ventilation is taken as 95% of the longterm average ventilation. The instantaneous ventilation is fed as the input signal to a clipped integral controller, with the target ventilation as the reference signal. The output of the controller determines the degree of ventilatory support. Clipping is typically to between half and double the degree of support that would do all the respiratory work. A third measure of ventilation, for example instantaneous ventilation low pass filtered with a time constant of 5 seconds, is calculated. Ventilatory support is in phase with the subject's respiratory airflow to the fuzzy extent that this ventilation is above target, and at a preset rate conversely.

22 Claims, 7 Drawing Sheets

U.S. PATENT DOCUMENTS

| | | | |
|---|---|---|---|
| 5,598,838 A * | 2/1997 | Servidio et al. | 128/204.23 |
| 5,704,345 A * | 1/1998 | Berthon-Jones | 128/204.23 |
| 5,740,795 A | 4/1998 | Brydon | |
| 5,794,615 A | 8/1998 | Estes | |
| 5,845,636 A * | 12/1998 | Gruenke et al. | 128/204.23 |
| 5,957,861 A | 9/1999 | Combs et al. | |
| 5,974,340 A | 10/1999 | Kadhiresan | |
| 6,041,780 A | 3/2000 | Richard et al. | |
| 6,085,747 A | 7/2000 | Axe et al. | |
| 6,105,575 A | 8/2000 | Estes et al. | |
| 6,305,372 B1 * | 10/2001 | Servidio | 128/204.21 |
| 6,336,454 B1 * | 1/2002 | Farrell et al. | 128/200.24 |
| 6,363,933 B1 * | 4/2002 | Berthon-Jones | 128/204.23 |
| 6,532,959 B1 * | 3/2003 | Berthon-Jones | 128/204.23 |

FOREIGN PATENT DOCUMENTS

WO    WO 98/12965    4/1998

* cited by examiner

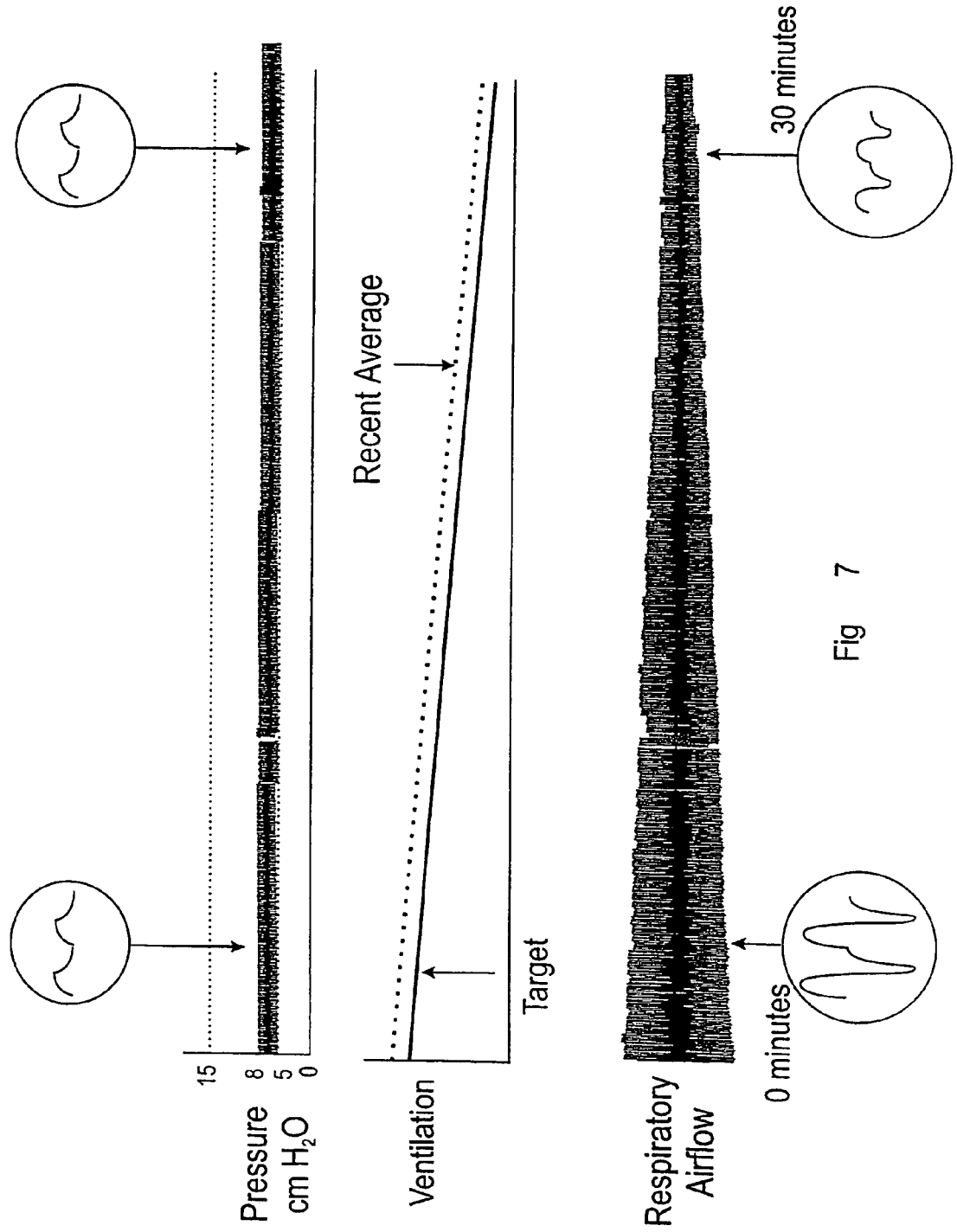

VENTILATORY ASSISTANCE FOR TREATMENT OF CARDIAC FAILURE AND CHEYNE-STOKES BREATHING

This is a continuation of application Ser. No. 10/374,487 filed Feb. 26, 2003, which is a continuation of application Ser. No. 09/316,432, now U.S. Pat. No. 6,532,959, incorporated herein by reference.

FIELD OF THE INVENTION

The invention relates to methods and apparatus for the provision of positive pressure ventilatory assistance for patients with cardiac failure or Cheyne-Stokes breathing from any cause, including central sleep apnea, cardiac failure or stroke.

EXPLANATION OF TERMS

In this specification, respiratory airflow is intended to refer to the instantaneous flow of gas into or out of the lungs. The term "average" is intended to mean any measure of central tendency or the result of any low pass filtering operation. Ventilatory support is intended to mean any procedure which has a similar effect as the respiratory muscles, particularly the supply of breathable gas under varying positive pressure to the airway via a nosemask, face mask, endotracheal tube, tracheotomy tube, or the like, but also including other procedures such as negative pressure ventilation, cuirasse, iron lung, external chest compression, or rocking bed ventilation. According to common usage, ventilation can mean either a procedure, as in the expression "positive pressure ventilation", or a measure of average respiratory airflow over a period of time. Instantaneous ventilation is intended to mean the volume inspired over a short period of time less than several seconds. Equally it can be calculated as the volume expired over such a period, or it can be the average of the two. For example, measures of instantaneous ventilation would include half the average of the absolute value of the respiratory airflow, calculated over a time interval short compared with several seconds, or half the absolute value of the respiratory airflow, low pass filtered with a time constant short compared with several seconds. For technical reasons to be explained below, in the best embodiment, instantaneous ventilation is taken as half the absolute value of the instantaneous respiratory airflow, ie averaged over an arbitrarily short period of time. However, it is not intended that the invention is limited to calculating instantaneous ventilation in this way.

The term "varying A inversely with B" is intended in the broad sense of increasing A if B is decreasing, and decreasing A if B is increasing.

The term "servo-controller" here refers to a feedback controller accepting an input, or controlled, variable (for example actual measured ventilation) and a reference quantity (for example a desired or target ventilation), and producing an output (for example the settings of a ventilator) which is used to subsequently bring the value of the input (controlled) variable towards the value of the reference variable.

The term "oppose" can include reduce, limit, dampen, or prevent.

The terms "recent average ventilation" and "longterm average ventilation" are to be understood to be equivalents.

BACKGROUND OF THE INVENTION

Patients with cardiac failure have reduced cardiac ejection fraction, are typically very breathless, and often wake at night with extreme breathlessness called paroxysmal nocturnal dyspnea, due to accumulation of fluid in the lungs.

Patients with cardiac failure also often have Cheyne-Stokes breathing, particularly during sleep. Cheyne-Stokes breathing is an abnormal limit cycle instability of the patient's respiratory controller in which there are rhythmic alternating periods of waxing and waning. ventilation, causing repetitive deoxygenation and reoxygenation of the arterial blood. The cause of the waxing and waning of ventilation is not entirely clear, but there is an increase in chemoreceptor gain [Wilcox I et al. *Ventilatory control in patients with sleep apnoea and left ventricular dysfunction: comparison of obstructive and central sleep apnoea.* 1998; 11:7–13], possibly related to stimuli arising in the heart or lungs, a change in the chemoreceptor set point leading to overventilation and alkalosis in the awake state with apneas during sleep, and an increase in circulation time leading to delays between ventilation arid chemoreception [Naughton M et al. *Role of hyperventilation in the pathogenesis of central sleep apneas in patients with congestive heart failure. Am Rev Respir Dis* 1993; 148:330–338]. Cheyne-Stokes breathing is associated with high mortality [Andreas et al. *Cheyne-Stokes respiration and prognosis in congestive heart failure. Am J Cardiol* 1996; 78:1260–1264]. It is possible that it is harmful because of the repetitive hypoxia, which will lead to hypoxic pulmonary vasoconstriction and high right heart afterload, and to increased sympathetic activity, systemic vasoconstriction and high left heart afterload. It may also be harmful because of repetitive alkalosis during the waxing period of the cycle. Finally, in some patients it is associated with repetitive arousal from sleep, which causes severe sleep disruption, increased sympathetic activity, and increased afterload.

Continuous positive airway pressure (CPAP) has been used for decades for the emergency treatment of pulmonary oedema, and is more recently being used longterm during sleep for the treatment of cardiac failure. Nasal CPAP leads to an improvement in cardiac output and ejection fraction, and an improvement in quality of life [Naughton M T et al, *Treatment of congestive heart failure and Cheyne-Stokes respiration during sleep by continuous positive airway pressure. Am J Respir Crit Care Med* 1995; 151:92–97], and a reduction in sympathetic nervous system activity [Naughton M T et al, *Effects of nasal CPAP on sympathetic activity in patients with heart failure and central sleep apnea Am J Respir Crit Care Med* 1995; 152:473–479]The precise mechanism of action is unclear. Making the alveolar pressure and right atrial pressure positive with respect to the inferior vena caval pressure, and making the left ventricular pressure more positive with respect to abdominal aortic pressure, will tend to dry the lungs, improve gas exchange, relieve paroxysmal nocturnal dyspnea, reduce reflex pulmonary vasoconstriction, reduce sympathetic activity and reduce cardiac afterload via multiple complex mechanisms. Standard nasal CPAP masks may also help stabilize Cheyne-Stokes breathing, because the effective ventilation cannot exceed the fresh gas flow, which is in turn set by the exhaust flow. Finally, many patients with cardiac failure also have coexisting obstructive sleep apnea, which worsens cardiac failure but is treated by nasal CPAP.

Unfortunately, despite excellent effectiveness, nasal CPAP is often poorly tolerated by patients with cardiac failure, particularly early on in treatment, and it has not become widely used. The reasons for the poor tolerance are unknown. In addition, nasal CPAP reduces, but unfortunately does not immediately suppress the Cheyne-Stokes breathing [Naughton M T et al. *Effect of continuous positive airway pressure on central sleep apnea and nocturnal PCO2 in heart failure. Am J Respir Crit Care Med* 1994; 150: 1598–1604].

Various other approaches using known methods of ventilatory assistance suggest themselves in order to provide the same benefit as CPAP while also reducing either respiratory work or Cheyne-Stokes breathing or both. Unfortunately no known device is completely satisfactory, either because of discomfort, overventilation, or both. For example, FIG. 1 shows persistent Cheyne-Stokes breathing in a patient with cardiac failure being treated with bilevel ventilatory support with timed backup. The subject is in stage 3 non-REM sleep. The polygraph tracings are arterial haemoglobin oxygen saturation (top tracing), chest wall movement (middle tracing), and mask pressure (bottom tracing). The Cheyne-Stokes breathing persists. Note, in the middle trace, the cyclical waxing and waning of the amplitude of chest wall movement, indicating periods of overbreathing and underbreathing, and resultant regular decreases in arterial haemoglobin oxygen saturation despite the ventilatory support.

Many classes of ventilator, far from increasing comfort, actually decrease comfort. Volume cycled ventilators (regardless of the trigger variable) and time triggered ventilators (regardless of the cycling variable) often show very poor synchronization between machine and patient, which is distressing to the patient. Volume cycled ventilators and high impedance pressure cycled ventilators do not permit the patient to increase or decrease ventilation voluntarily, which is also distressing to the patient. Subjects with Cheyne-Stokes breathing may be particularly distressed by inadequate volume settings, due to their high chemoreceptor gain.

Another serious problem is overventilation. Most ventilatory assistance devices are designed to replace or augment respiratory effort in subjects with respiratory failure or insufficiency, and by design, cause a nett increase in mean ventilation above the subject's spontaneous mean ventilation. Unfortunately, in subjects who are not initially acidotic, such as the subjects of the present discussion, ventilatory assistance causes or exacerbates hypocapnia and alkalosis, leading in turn to reflex upper airway and particularly vocal cord closure during sleep [Jounieux et al. *Effects of nasal positive pressure hyperventilation on the glottis in normal sleeping subjects. J Appl Physiol* 1995; 79:186–193]. Far from treating the disordered breathing, excessive ventilatory support will actually produce closed airway central apneas. Some ventilatory assistance devices, in an attempt to provide increased comfort, support ventilation specifically during periods of increased patient effort (for example proportional assist ventilation and all classes of ventilators with spontaneous triggering without timed backup). This will yet further enhance any tendency to cyclically disordered breathing during sleep. Similarly, in the case of volume cycled ventilators, awake comfort can usually only be achieved by overventilation, with alkalosis and consequent airway closure in sleep. Overventilation and alkalosis can sometimes be extremely dangerous. Indeed, in patients with cardiac failure and acute pulmonary edema, bilevel ventilation with fixed high pressure swings appears to be associated with an increased risk of myocardial infarction [Mehta et al. *Randomized prospective trial of bilevel versus continuous positive airway pressure in acute pulmonary oedema. Crit Care Med* 1997; 25:620–628].

Another approach to the overventilation problem is to provide ventilatory assistance only during periods of reduced subject efforts, for example by triggering the ventilator only if the subject has not produced an inspiration for at least a specified period of time. This is unsatisfactory for three reasons. Firstly, during spontaneous breathing, this solution will not provide any increase in comfort over normal CPAP, and this was one of the problems to be solved. Secondly, the sudden abrupt increase in support at the onset of an apnea will in general tend to awaken the patient from sleep, leading to both sleep fragmentation and transient overventilation leading to further sleep disordered breathing. Thirdly, as with all previous methods, it is difficult to set the level of support during periods of central apnea high enough to prevent Cheyne-Stokes breathing or central sleep apneas, but not so high as to produce airway closure.

A more satisfactory approach is described in commonly owned International Publication No. WO 98/12965, in which a target ventilation is selected, and the degree of support is automatically adjusted to servo-control the measured ventilation to at least equal the target ventilation. A minimum level of support, chosen not to produce overventilation, is provided for comfort during awake breathing. If the target ventilation is chosen to be slightly less than the eupneic ventilation, then Cheyne-Stokes breathing and central sleep apnea may be prevented without the risk of overventilation. Because the degree of support increases smoothly as the subject's own efforts decrease, there is no explosively sudden increase in support which might wake the patient. However, there are two limitations to having a fixed target ventilation. Firstly, the target ventilation needs to be chosen, and this can be difficult: too high a value will lead to overventilation, while too low a value will permit some residual Cheyne-Stokes breathing. Secondly, due to changes in metabolic rate with restlessness, sleep state, body temperature, meals, etc, the ideal target ventilation is not constant.

In summary, longterm nasal CPAP therapy is of known benefit in the treatment of cardiac failure, but is poorly tolerated, and does not usually or completely alleviate Cheyne-Stokes breathing or central sleep apnea, at least initially. Attempting to increase tolerance and/or treat the disordered breathing using ventilatory support is difficult, or only partially successful, depending on the device used, because of the need to avoid overventilation. Very similar comments apply to the treatment of Cheyne-Stokes breathing and/or central sleep apnea due to many other causes in such as stroke or acromegaly.

DISCLOSURE OF THE INVENTION

The present invention is directed to providing a subject with cardiac failure positive airway pressure therapy, to achieve an improvement in the symptoms and signs of cardiac failure similar to that afforded by CPAP, by modulating the mask pressure in such a way as to provide increased comfort without overventilation, hypocapnia, alkalosis, or upper airway closure. The present invention is further directed to the stabilization or prevention of Cheyne-Stokes breathing or central sleep apnea from many causes.

The invention discloses a method for treatment of cardiac failure, Cheyne-Stokes breathing, or central sleep apnea, comprising the steps of:

providing a subject with ventilatory support;
deriving a measure of instantaneous ventilation; and
adjusting the degree of ventilatory support to oppose short term changes in said measure of instantaneous ventilation, but permitting longterm changes in said measure of instantaneous ventilation.

The invention further discloses apparatus for the treatment of cardiac failure, Cheyne-Stokes breathing or central sleep apnea, comprising:
  a device for providing ventilatory support of controllable magnitude;
  means for deriving a signal indicative of instantaneous ventilation of a subject; and
  a servo-controller operable to control the degree of ventilatory support provided by said ventilatory support device to oppose short-term changes in said measure of instantaneous ventilation, but permit longterm changes in said measure of instantaneous ventilation.

The invention discloses a method for treatment of cardiac failure, Cheyne-Stokes breathing or central sleep apnea, comprising the steps of:
  providing a subject with ventilatory support;
  deriving a measure of the subject's instantaneous ventilation; and
  adjusting the degree of ventilatory support to reduce changes in said measure of instantaneous ventilation over a timescale similar to that of the waxing-waning cycle of untreated Cheyne-Stokes breathing or central sleep apnea, while allowing changes in said measure of instantaneous ventilation over a timescale much longer than said waxing-waning cycle.

The invention further discloses a method for treatment of cardiac failure, Cheyne-Stokes breathing or central sleep apnea, comprising the steps of:
  providing a subject with ventilatory support;
  deriving a measure of the subject's instantaneous ventilation;
  deriving a measure of the subject's longterm average ventilation;
  setting the controlled variable of a servo-controller to a function of said measure of the subject's instantaneous ventilation;
  setting the reference variable of said servo-controller to a measure of the subject's longterm average ventilation; and
  adjusting the magnitude of said ventilatory support in accordance with the output of said servo-controller.

The invention yet further discloses a method for treatment of cardiac failure, Cheyne-Stokes breathing or central sleep apnea, comprising the steps of:
  providing a subject with ventilatory support;
  deriving a measure of the subject's instantaneous ventilation;
  high pass filtering said measure of the subject's instantaneous ventilation; and
  adjusting the degree of said ventilatory support inversely with said high pass filtered measure of the subject's instantaneous ventilation.

The invention also discloses a method for the treatment of cardiac failure, Cheyne-Stokes breathing or central sleep apnea, comprising the steps of:
  providing a subject with positive pressure ventilatory support, with controllable amplitude and rate;
  deriving a measure of the subject's instantaneous ventilation;
  adjusting said amplitude of positive pressure by:
    (a) low pass filtering said measure of instantaneous ventilation to derive a measure of recent average ventilation;
    (b) setting a target ventilation equal to a fraction of said measure of recent average ventilation; and
    (c) servo-controlling said measure of instantaneous ventilation to at least equal the target ventilation, by adjusting the degree of ventilatory support;
  and
  continuously adjusting said rate by:
    (a) to the extent that the instantaneous ventilation equals or exceeds said target ventilation, modulating said positive pressure in phase with respiratory airflow; and
    (b) to the extent that the instantaneous ventilation is less than said target ventilation, modulating said positive pressure at a pre-set rate.

The invention further discloses apparatus for treatment of cardiac failure, Cheyne-Stokes breathing or central sleep apnea, comprising:
  a controllable source of breathable gas at positive pressure;
  means for delivering said breathable gas at positive pressure to a subject's airway;
  means for deriving a measure of the subject's instantaneous ventilation; and
  a servo-controller for adjusting the degree of ventilatory support to reduce changes in said measure of instantaneous ventilation over a timescale similar to that of the waxing-waning cycle of untreated Cheyne-Stokes breathing or central sleep apnea, while allowing changes in said measure of instantaneous ventilation over a timescale much longer than said waxing-waning cycle.

The invention yet further discloses apparatus for treatment of cardiac failure, Cheyne-Stokes breathing or central sleep apnea, comprising:
  a controllable source of breathable gas at positive pressure;
  means for delivering said breathable gas at positive pressure to a subject's airway;
  means for deriving a measure of the subject's instantaneous ventilation;
  means for deriving a measure of the subject's longterm average ventilation;
  means for deriving a target ventilation as a function of said measure of the subject's longterm average ventilation;
  a servo-controller, whose input variable is a function of said measure of the subject's instantaneous ventilation, and whose reference variable is said target ventilation; and
  means for adjusting the magnitude of said ventilatory support according to the output of the servo-controller.

The invention also discloses apparatus for the treatment of cardiac failure, Cheyne-Stokes breathing or central sleep apnea, comprising:
  ventilator means for providing ventilatory support with controllable amplitude and rate;
  sensor and processing means for deriving a signal indicative of instantaneous ventilation of a subject; and
  servo-control means operable to adjust the amplitude of the pressure support by low pass filtering said instantaneous ventilation signal to derive a measure of recent average ventilation, setting a target ventilation equal to a fraction of said measure of recent average ventilation, and servo-controlling said measure of instantaneous ventilation to at least equal the target ventilation, and further operable to continuously adjust said rate by modulating said positive pressure in phase with respiratory airflow to the extent that the instantaneous ventilation equals or exceeds said target ventilation, and modulating said positive pressure at a pre-set rate to the extent that the instantaneous ventilation is less than said target ventilation.

Embodiments of the invention provide a degree of ventilatory support which many subjects will perceive as very comfortable. Cheyne-Stokes breathing is reduced or eliminated. Unlike the case of prior art taught in International Publication No. WO 98/12965, the physician is not required to estimate or empirically determine a target ventilation, as this is done automatically. The risk of overventilating the subject and causing alkalosis or airway closure is also reduced.

BRIEF DESCRIPTION OF THE DRAWINGS

Embodiments of the present invention will now be described, by way of example only, with reference to the accompanying drawings.

FIG. 7 is a schematic diagram showing, for the preferred embodiment, how the degree of assistance will remain at the minimum level if the subject's ventilation steadily decreases over a very long time period.

DESCRIPTION OF PREFERRED
EMBODIMENTS AND BEST MODE

Figure 2:
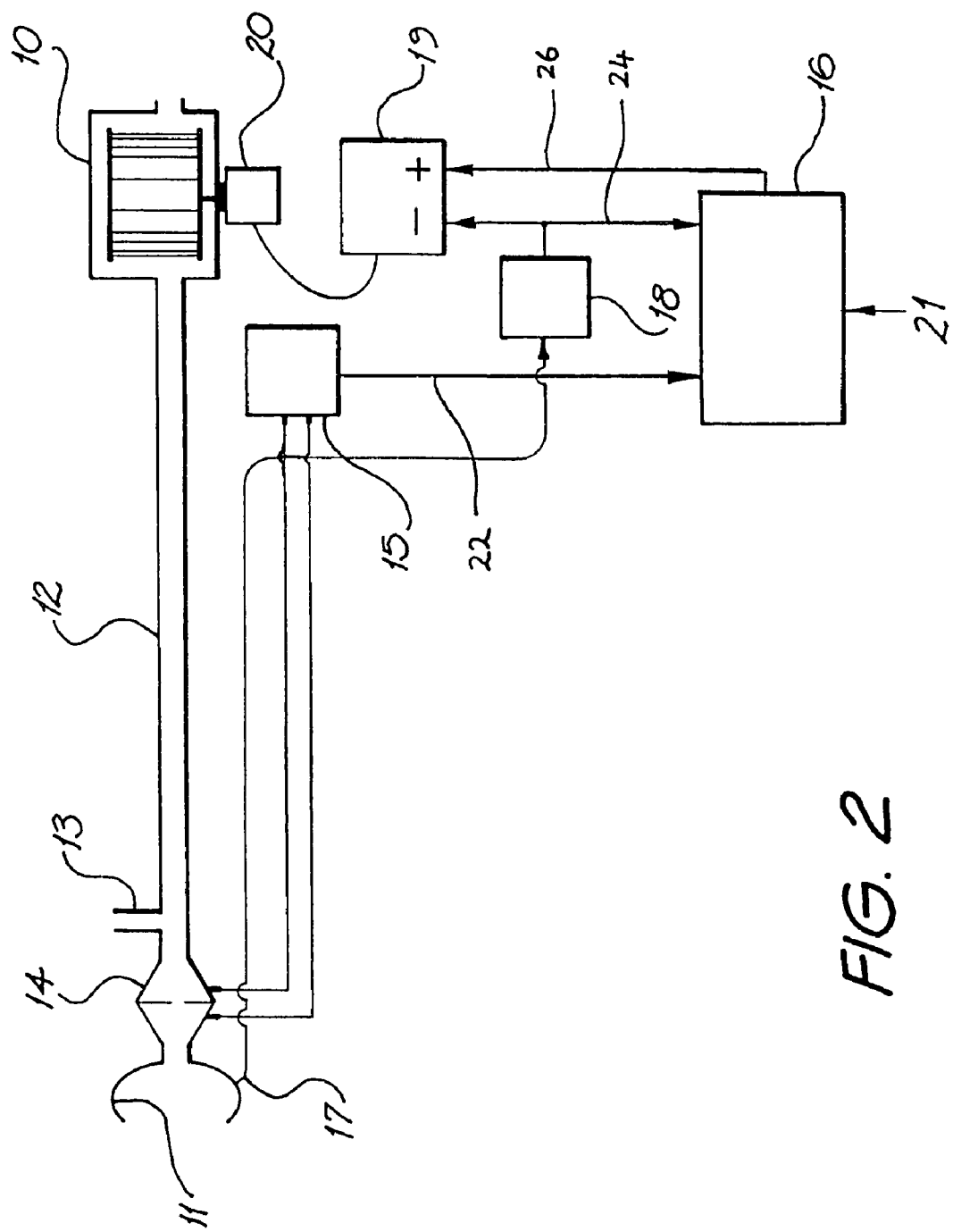
FIG. 2 is a schematic diagram of ventilation apparatus embodying the invention.

A ventilator embodying one form of the invention is shown in FIG. 2 in which a blower 10 supplies breathable gas to a mask 11 for communication with a subject's airway via a delivery tube 12 and exhausting to atmosphere via an exhaust 13. Airflow at the mask 11 is measured using a pneumotachograph 14 and a differential pressure transducer 15. The mask flow signal 22 from the transducer 15 is sampled by a microcontroller 16. Mask pressure is measured at port 17 using a pressure transducer 18. The pressure signal 24 from the transducer 18 is also sampled by the microcontroller 16. The microcontroller 16 sends an instantaneous mask pressure request signal 26 to a servo 19, which compares the pressure request signal (ie. the desired pressure signal) 26 with the actual pressure signal 24 from the transducer 18 to control a motor 20 driving the blower 10. The microcontroller 16 settings can be adjusted via a serial port 21.

It is to be understood that the mask could equally be replaced with a tracheotomy tube, endotracheal tube, nasal pillows, or other means of making a sealed connection between the air delivery means and the subject's airway.

The steps performed by the microcontroller 16 to determine the requested mask pressure will now be described.

The microcontroller 16 accepts the mask airflow and pressure signals 22,24, and from said signals determines the instantaneous flow through any leak between the mask and subject, by any convenient method. For example, the conductance of the leak may be estimated as the instantaneous mask airflow low pass filtered with a time constant of 10 seconds, divided by the similarly low pass filtered square root of the instantaneous mask pressure, and the instantaneous leakage flow may be calculated as said conductance multiplied by the square root of the instantaneous mask pressure. Respiratory airflow is then calculated as the instantaneous mask airflow minus said instantaneous leakage flow.

Having determined the respiratory airflow, the microcontroller 16 now determines the subject's recent average absolute respiratory airflow as the 100 second low pass filtered absolute value of the respiratory airflow. The 100 second time constant is chosen because it is long compared with the lung-chemoreceptor delay in patients with Cheyne-Stokes breathing or central sleep apnea (typically up to 20 sec), and somewhat longer than the cycle time of typical Cheyne-Stokes breathing of about 60 seconds. Longer time constants will in principle give better suppression of Cheyne-Stokes breathing as long as the subject's chemoreceptor set-point is constant, but will take longer to settle at sleep onset and longer to track changes in set-point. The term "recent average" is used in the sense of recent compared with an entire night's sleep. However, compared with "instantaneous" ventilation, which is measured on a timescale of a single breath or less, the 100 second low pass filtered absolute value of the respiratory airflow is, of course, a longterm average.

A target absolute respiratory airflow is then calculated as 95% of said recent average absolute respiratory airflow. Larger values can result in positive feedback leading to drift in the ventilation, while smaller values will permit residual Cheyne-Stokes breathing.

Figure 5:
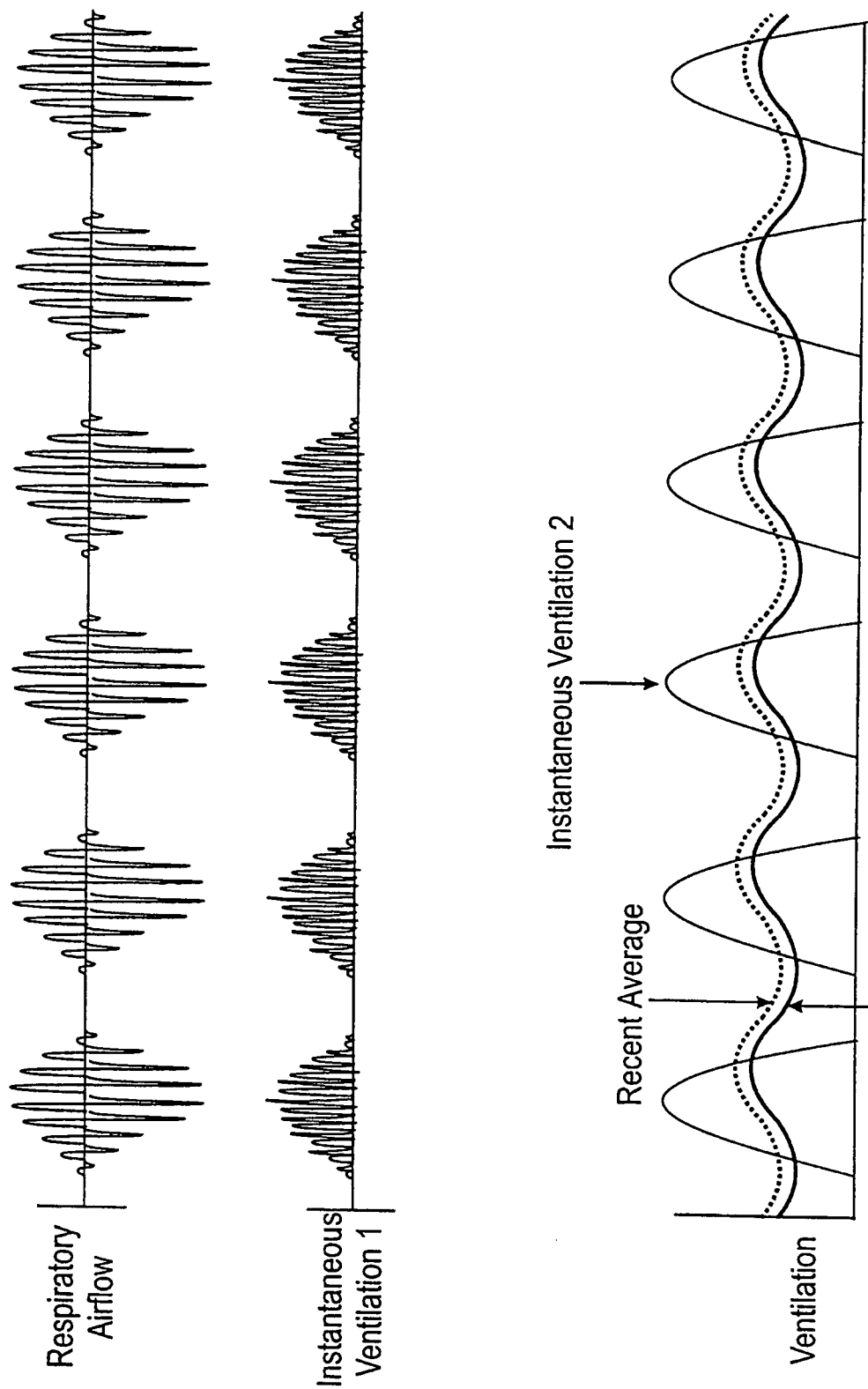
FIG. 5 is a schematic diagram showing respiratory airflow during Cheyne-Stokes breathing, and various calculated quantities, including two measures of "instantaneous" ventilation, "recent average" ventilation, and "target" ventilation with time.

FIG. 5 shows the above steps schematically. The top tracing in the figure is respiratory airflow. The second tracing, labelled "Instantaneous Ventilation 1", is the absolute value of the respiratory airflow. The bottom tracing shows, schematically, another measure of instantaneous ventilation, labelled "Instantaneous Ventilation 2", which is Instantaneous Ventilation 1 low pass filtered with a time constant of a few breaths. Instantaneous Ventilation 2, as a measure of ventilation, could equally be subsequently used as an input to a servo-controller to adjust the degree of ventilatory support, although this may not be the optimal approach. The bottom tracing also shows schematically the recent average ventilation and the target ventilation.

Having calculated the target ventilation, a microcontroller now calculates a mask pressure modulation amplitude A. The object of this step is to modulate the pressure modulation amplitude in a direction opposite to changes in the output from the subject's own respiratory controller, providing more support when the subject is making shallow efforts, and less support when the subject is making strong efforts, thus stabilizing the subject's breathing. It is necessary in this step that the servo-controller should have a delay that is very short compared with the delay in the subject's own respiratory controller; a long delay would further destabilize the subject's breathing. If a proportional or integral controller were fed with a measure of the subject's ventilation taken over many seconds, for example, longer than the case of "Instantaneous Ventilation 2" in FIG. 5, the controller delay would be too long. Conversely, if a proportional controller were supplied with the rectified instantaneous respiratory airflow (as in Instantaneous Ventilation 1 in FIG. 5), then the controller output would be varying out of phase with the subject's breathing efforts, and the subject would perceive an increase in the work of breathing. In the present implementation, a clipped integral controller is fed with Instantaneous Ventilation 1, the absolute value of the respiratory airflow. The process of integration both smooths and delays within-breath changes in the amplitude A, so that the subject does not perceive any increase in work of breathing. A suitable algorithm is as follows:

calculate an error term e equal to the instantaneous absolute respiratory airflow minus the target absolute respiratory airflow;

set the pressure modulation amplitude A equal to $$A = \int Gedt$$

where G is the controller integral gain, typically −0.3 cmH$_2$O L/min per second, and the integral A is clipped to a convenient range such as 3–12 cmH$_2$O.

Larger values of G can result in positive feedback in the controller. Smaller values will permit some residual untreated Cheyne-Stokes breathing or central sleep apnea. The minimum amplitude (3 cmH$_2$O being a suitable value suitable for most subjects) is chosen to be of the order of 50% of the estimated amplitude required to perform all the respiratory work of the subject in the steady state. A minimum value of this order of magnitude provides much improvement in comfort over a minimum value of zero. The maximum amplitude (12 cmH$_2$O being typical) is chosen to be approximately double the amplitude that would perform all the respiratory work of the subject (and therefore sufficient to support the subject's breathing if they cease making any efforts) but less than a value that would be uncomfortable or dangerous.

The microcontroller 16 then determines the instantaneous phase $\Phi$ in the respiratory cycle from the instantaneous respiratory airflow, looks up a pressure waveform template $\Pi(\Phi)$ and sets the instantaneous mask pressure to:

$$P_{mask} = P_0 + A\Pi(\Phi)$$

where $P_0$ is an end expiratory pressure, typically 5–10 cmH$_2$O, but chosen to be sufficient to treat any underlying obstructive sleep apnea syndrome.

In a simplest embodiment, the respiratory phase $\Phi$ is taken as bivalued: inspiratory if the instantaneous respiratory airflow is positive, and expiratory otherwise, and $\Pi(\Phi)$ is unity for inspiration and zero for expiration. If phase has been expiratory for more than a set time, chosen to be slightly longer than the subject's normal expiratory time, then the phase is switched to inspiratory.

Figure 3:
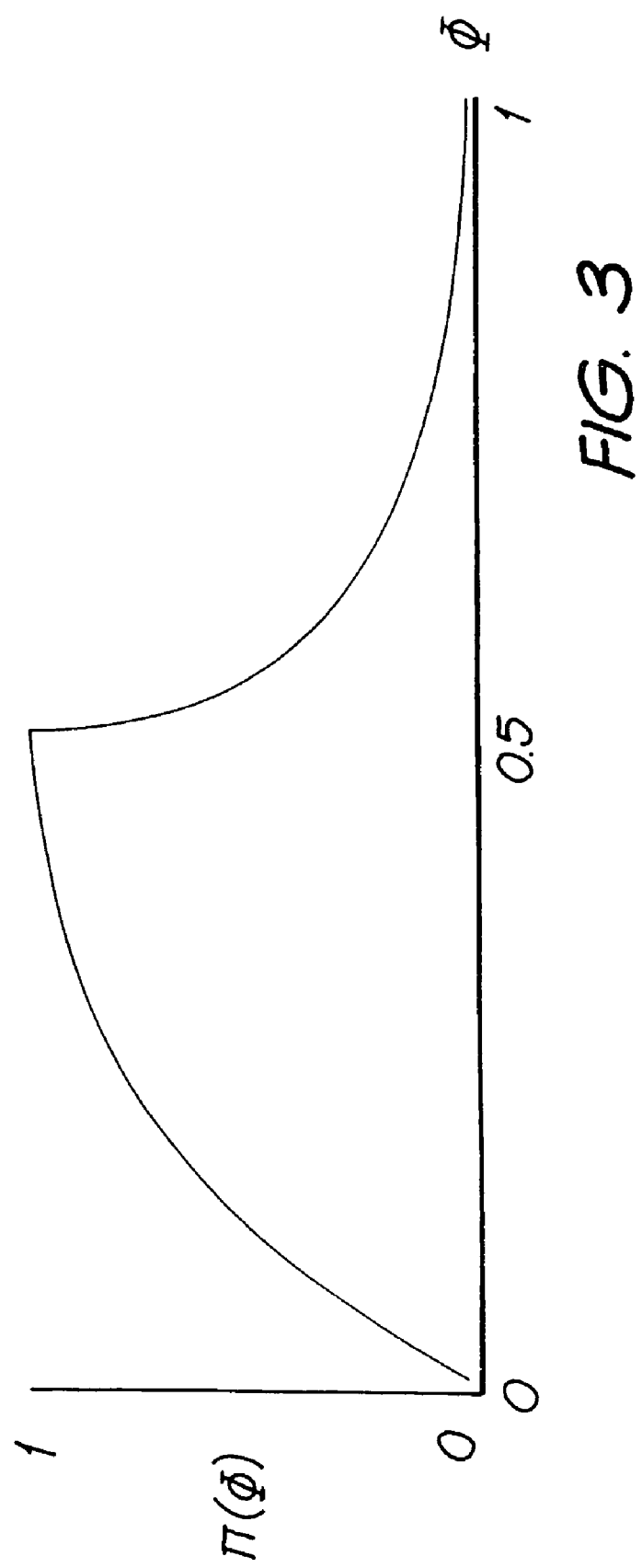
FIG. 3 is a plot of a pressure waveform template. The horizontal axis $\phi$ is the phase in the respiratory cycle, measured in revolutions, such that 0 is start of inspiration, 0.5 revolutions is start of expiration, and 1 revolution is end of expiration.

In another embodiment, $\Phi$ is a continuous variable from zero to 1 revolution, and the pressure waveform template $\Pi(\Phi)$ is as shown in FIG. 3, In this embodiment, the microcontroller determines $\Phi$ using the following fuzzy logic rules:

1. If the airflow is zero and increasing fast then the phase is 0 revolutions.
2. If the airflow is large positive and steady then the phase is 0.25 revolutions.
3. If the airflow is zero and falling fast then the phase is 0.5 revolutions.
4. If the airflow is large negative and steady then the phase is 0.75 revolutions.
5. If the airflow is zero and steady and the 5 second low pass filtered absolute value of the respiratory airflow is large then the phase is 0.9 revolutions.
6. If the airflow is positive and the phase is expiratory, then the phase is 0 revolutions.
7. If the airflow is negative and the phase is inspiratory, then the phase is 0.5 revolutions.
8. If the 5 second low pass filtered absolute value of the respiratory airflow is small, the phase in the respiratory cycle is increasing at a fixed rate equal to the subject's expected respiratory rate.
9. If the 5 second low pass filtered absolute value of the respiratory airflow is large, the phase in the respiratory cycle is increasing at a steady rate equal to the existing rate of change of phase, low pass filtered with a time constant of 20 seconds.

The fuzzy extent to which the airflow is "large", "steady", etc can be determined with suitable membership functions.

Rules 1–4 estimate the phase directly from the instantaneous respiratory airflow. Rule 5 permits an expiratory pause, whose length may be long if the subject has recently been breathing adequately, and short or zero if the subject is not breathing. This is particularly appropriate for subjects with Cheyne-Stokes breathing, because an expiratory pause should not be permitted if the subject is apneic. Rules 6–7 provide for quick resynchronization in the event that the subject breathes irregularly. Rule 8 provides the equivalent of a timed backup, in which, to the extent that the subject has stopped breathing or is not adequately breathing, the ventilator will cycle at a suitable fixed rate. Rule 9 provides that to the extent that the subject is breathing adequately, the ventilator will tend to track the subject's recent average respiratory rate. This is particularly appropriate in subjects with cardiac failure and Cheyne-Stokes breathing, whose respiratory rate tends to be extremely steady despite rhythmic changes in amplitude.

An effect of the changing degree of activation of rules 8 and 9 is that, to the fuzzy extent that the instantaneous ventilation equals or exceeds the target ventilation, ventilatory support will be provided in phase with the subject's own respiratory efforts, and to the extent that the instantaneous ventilation is less than the target ventilation, ventilatory support will be provided at a pre-set rate.

In an elaboration of this embodiment, the weighting of rules 1–6 can be made proportional to the fuzzy extent that the instantaneous ventilation is large compared with the target ventilation. This strengthens the tendency for the device to act as described in the previous paragraph.

In a further elaboration, the weighting of rules 1–6 and also of rule 9 can be made smaller, and the weighting of rule 8 can be larger, if the leak is large, or if there is a sudden change in the leak. In this way, to the extent that the respiratory airflow signal is of high quality, ventilatory support will be provided as described in the preceding paragraphs, but to the extent that the respiratory airflow signal is of poor quality and it is difficult to synchronize reliably with the patient's efforts, or to know if the patient's efforts are adequate, ventilatory support will be provided in an orderly manner at a predetermined fixed rate.

Assuming that the sleeping subject's PCO$_2$ is stable at slightly above the subject's chemoreceptor set-point and the airway is open, the system will remain stable. This is explained as follows. The minimum amplitude, A, of 3 cmH$_2$O will be unloading some of the subject's high work of breathing, but is too small to provide all the respiratory work needed to maintain ventilation and PCO$_2$ at the subject's set-point. Therefore, there will be an error signal from the subject's chemoreceptors. Therefore the subject will be making spontaneous ventilatory efforts (but less than usual), and the upper airway will be patent. Since the target ventilation is only 95% of the spontaneous ventilation, the actual ventilation will be slightly higher than the target ventilation, and the integrator determining amplitude A will remain clipped at the minimum amplitude. If there is a primary reduction in the subject's ventilation of more than 5% due to a primary reduction in ventilatory effort or increase in airway resistance, there will be an immediate and rapid increase in the amplitude A by sufficient to maintain ventilation at a level of at least 95% of the previous spontaneous level, thus preventing hypopneas.

Figure 6:
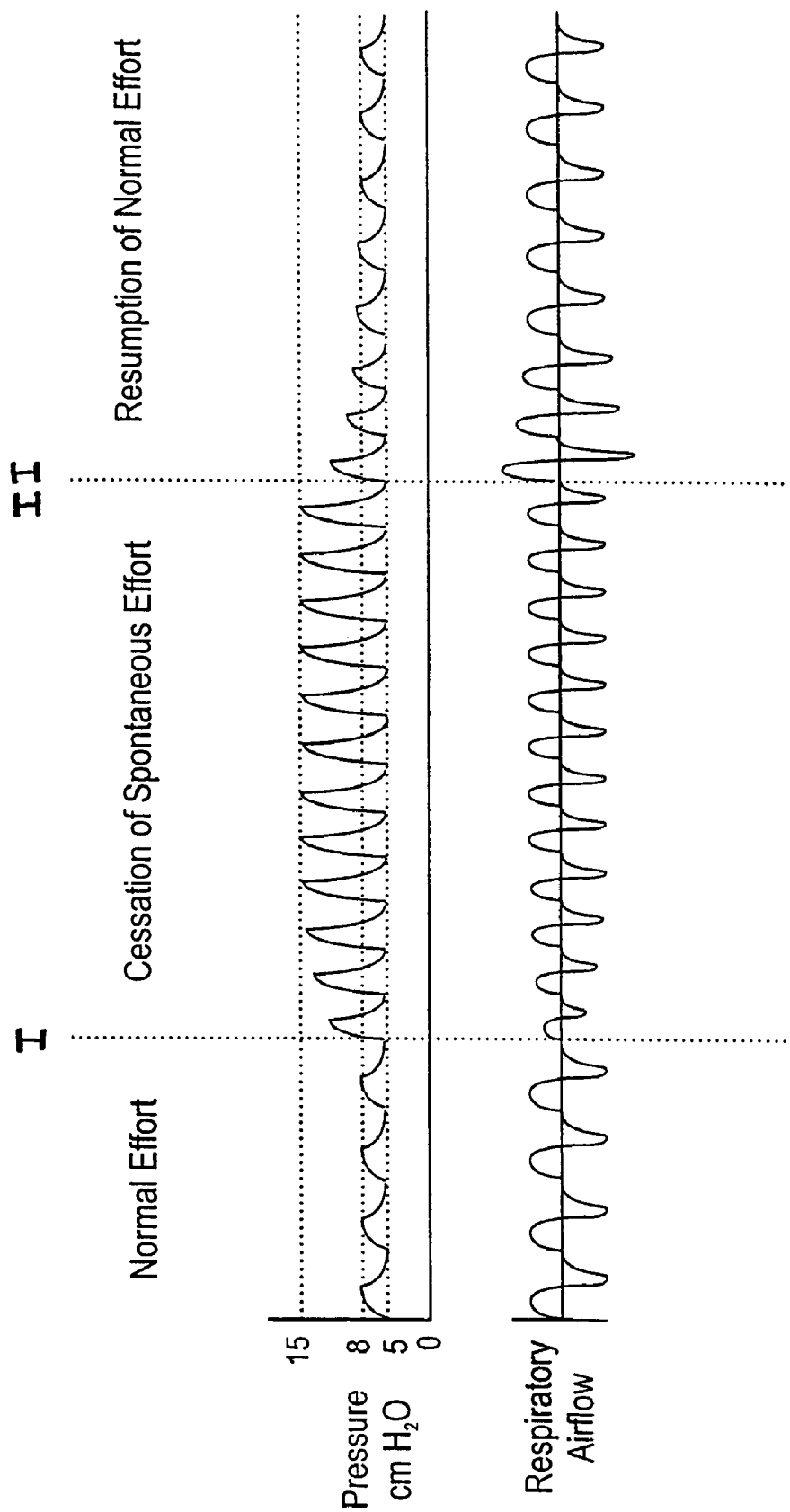
FIG. 6 is a schematic diagram showing, for a preferred embodiment, the expected increase in degree of ventilatory support in response to a sudden cessation of all respiratory efforts by the subject with time.

An example is shown schematically in FIG. 6. For the first 4 breaths, the subject is making steady respiratory efforts, and the pressure modulation amplitude A remains at the minimum value of 3 cmH$_2$O. Respiratory airflow is due to the combined efforts of subject and ventilation apparatus. At the first vertical line, I, the subject's spontaneous efforts cease. For the next 12 breaths, all respiratory airflow is due only to the machine. The first breath is delivered approximately on schedule, but produces less respiratory airflow than usual, because only the minimum degree of support is provided. Over the next few breaths, the amplitude A quickly to the maximum of 10 cmH$_2$O, restoring respiratory airflow to almost its original level. At the second vertical line, II, the subject recommences spontaneous respiratory efforts at the previous level, and the degree of machine generated support quickly reduces again. It is to be noted in FIG. 6 that during a period of cessation of spontaneous effort, the subject will be ventilated at the preset respiratory rate, due to the operation of fuzzy rule 8. Conversely, during the periods of normal effort, support is provided in phase with the subject's efforts. These may be slower than the preset rate (as in FIG. 6) or they may be faster than the preset rate.

The subject can acutely increase their spontaneous ventilation at will. Transient increases in ventilation for example due to brief arousals will lead to a small degree of hypocapnia, but the resultant secondary reduction or cessation in subject's efforts will again be immediately matched by an increase in amplitude A sufficient to hold ventilation at a level of at least 95% of the previous steady level. Conversely, gradual changes in the subject's chemoreceptor set-point over minutes will result in gradual changes in target ventilation, which will remain at 95% of the subject's actual ventilation. This is shown schematically in FIG. 7. The lower tracing shows respiratory airflow gradually decreasing over a 30 minute period. The calculated recent average ventilation and target ventilation (middle trace) similarly decline over the thirty minutes. However, since the recent average ventilation is always larger than the target ventilation, the degree of support always remains at the minimum (top tracing).

An embodiment of the invention was tested in ten patients with severe cardiac failure and Cheyne-Stokes breathing during sleep. The target ventilation was initially set to 5–7.5 L/min, and the end expiratory pressure P$_0$ was set to 8 cmH$_2$O. The patients were tested on each one of a control night (no assistance), nasal oxygen at 2 L/min, CPAP (7–10 cmH$_2$O as tolerated, bi-level CPAP (ResMed VPAP-ST™ machine, with VPAP at 4 cmH$_2$O and IPAP at 12–18 cmH$_2$O as required, with the backup rate at 2 L/min below the spontaneous rate), and a prototype of the present applicant's Auto CS™ machine.

The apnea+hypopnea index (AHI), ASDA microarousal index (ARI), and percentage of time in slow wave (SWS) and REM sleep were calculated using standard procedures. The results are presented as mean±sem. The statistical analysis is repeated measures ANOVA after rank transform.

|  | Control | Oxygen | CPAP | VPAP-ST | Auto CS |
|---|---|---|---|---|---|
| AHI (hr$^{-1}$) | 43.3 ± 3.5$^+$ | 24.8 ± 3.2$^+$ | 24.1 ± 3.4$^+$ | 9.0 ± 1.3$^‡$ | 4.8 ± 0.9 |
| ARI (hr$^{-1}$) | 48.1 ± 3.6$^+$ | 34.7 ± 4.5$^+$ | 30.8 ± 3.5$^+$ | 18.4 ± 3.4 | 14.5 ± 2.6 |
| SWS (%) | 13.7 ± 2.8 | 19.8 ± 2.6 | 19.3 ± 3.5 | 20.8 ± 3.0 | 21.1 ± 2.7 |
| REM (%) | 10.5 ± 2.1$^+$ | 13.3 ± 2.4 | 12.2 ± 1.6$^‡$ | 15.3 ± 2.3 | 18.4 ± 0.6 |

$^‡$Auto CS P < 0.05, $^+$Auto CS P < 0.01.

Figure 1:
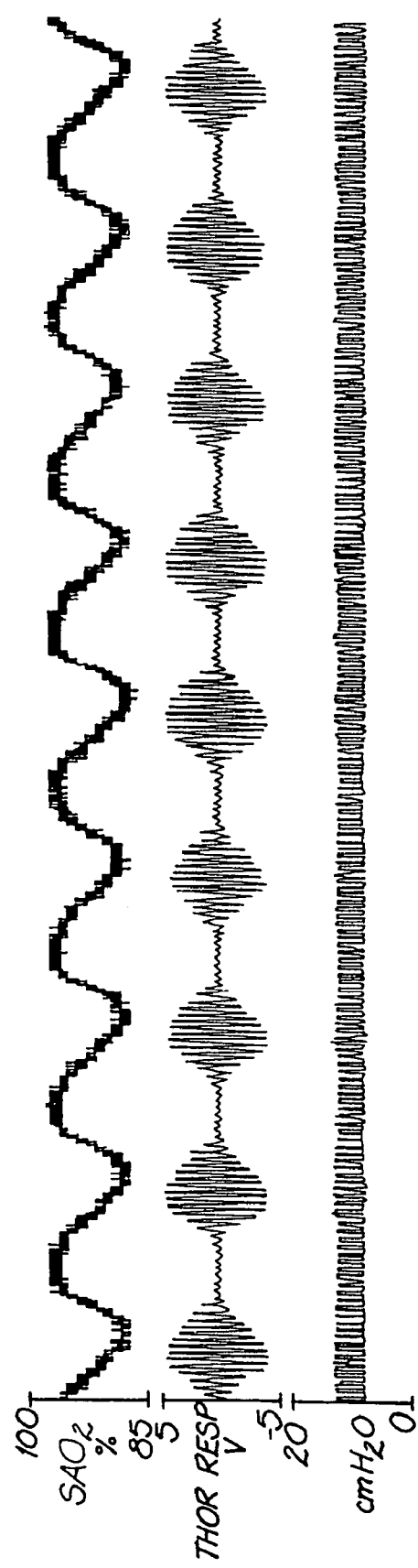
FIG. 1 is a plot of a 10 minute excerpt from a polygraph tracing from a sleeping patient with cardiac failure, during treatment with prior art bilevel ventilation in Stage III non-REM sleep.
Figure 4:
FIG. 4 is a plot of a 10 minute excerpt from a polygraph tracing from the subject from FIG. 1, also in Stage III non-REM sleep, being treated by an embodiment of the present invention. Cheyne-Stokes breathing has been eliminated.

In most subjects, transcutaneous PCO$_2$ fell by approximately 5–10 mmHg due to a period of hyperventilation in the first few minutes of awake breathing. This resulted in some instability of the upper airway and residual mild Cheyne-Stokes breathing for the first 20–40 minutes of sleep. Subsequently, Cheyne-Stokes breathing was largely abolished. FIG. 4 shows the same subject as FIG. 1, also in stage 3 non-REM sleep, but this time using the new device. The mask pressure swings are broadly comparable with those in FIG. 1, but very small changes with time can be seen, as the device opposes any changes in the subject's ventilation. It is clear that the subject's ribcage movement (ie. measured using a thoracic respiratory band) and oxygen saturation (SaO$_2$) are greatly stablized compared with FIG. 1, and Cheyne-Stokes breathing has been eliminated.

In some subjects, the period of unstable breathing immediately after sleep onset could be eliminated by asking the subject to remain awake for 20 minutes after applying the mask and before going to sleep, in order to minimize overbreathing immediately prior to sleep onset.

I claim:

1. A method for treatment of Cheyne-Stokes breathing during the provision of ventilatory support comprising the steps of:
    delivering a controlled supply of breathable gas at a pressure above atmospheric to a subject to provide the subject with ventilatory support during an inspiratory portion and an expiratory portion of a respiratory cycle of the subject;
    deriving a measure of respiratory airflow from the subject;
    selecting a ventilatory support target measure to oppose a Cheyne-Stokes pattern of breathing, said ventilatory support target measure being determined as a function of the measure of respiratory airflow; and
    modulating the degree of ventilatory support as a function of said ventilatory support target measure and said measure of respiratory airflow,
    wherein said ventilatory support counteracts a Cheyne Stokes waxing-waning pattern of breathing by changing pressure levels in the inspiratory portion and the expiratory portion, said changing pressure levels varying from previous pressure levels delivered in a previous inspiratory portion and a previous expiratory portion of a previous respiratory cycle of the subject.

2. The method of claim 1 wherein said degree of ventilatory support is a function of a comparison between said ventilatory support target measure and a further measure derived as a function of respiratory airflow.

3. The method of claim 2 wherein said further measure is derived on a time scale of less than a single breath.

4. The method of claim 3 wherein said ventilatory support target measure is a measure of ventilation.

5. The method of claim 4 wherein said further measure is instantaneous ventilation.

6. An apparatus for the treatment of Cheyne-Stokes breathing comprising:
   means for providing a breathable gas at a controllable pressure above atmospheric to a subject;
   means for deriving a flow signal indicative of a measure of respiratory airflow of the subject; and
   a controller to run said means for providing a breathable gas in response to said flow signal, wherein said controller comprises programmed instructions for execution by said controller, said instructions controlling steps of:
   delivering ventilatory support during an inspiratory portion and an expiratory portion of a respiratory cycle to the subject;
   determining a ventilatory support target measure as a function of the flow signal, said ventilatory support target measure being selected to oppose a Cheyne-Stokes pattern of breathing; and
   modulating the degree of ventilatory support to counteract a Cheyne-Stokes waxing-waning pattern of breathing by changing pressure levels in the inspiratory portion and the expiratory portion, said changing pressure levels varying from previous pressure levels delivered in a previous inspiratory portion and a previous expiratory portion of a previous respiratory cycle of the subject.

7. The apparatus of claim 6 wherein said degree of ventilatory support is a function of a comparison between said ventilatory support target measure and a further measure derived as a function of said flow signal.

8. The apparatus of claim 7 wherein said further measure is derived on a time scale of less than a single breath.

9. The apparatus of claim 8 wherein said ventilatory support target measure is a measure of ventilation.

10. The apparatus of claim 9 wherein said further measure is instantaneous ventilation.

11. A method for treatment of Cheyne-Stokes breathing during the provision of ventilatory support comprising the steps of:
    delivering a controlled supply of breathable gas at a pressure above atmospheric to a subject;
    deriving a measure of respiratory airflow from the subject;
    selecting a ventilatory support target measure to oppose a Cheyne-Stokes pattern of breathing, said ventilatory support target measure being determined as a function of the measure of respiratory airflow; and
    deriving an input value from said measure of respiratory airflow, said input value being derived during a time period less than that of one breath; and
    changing the degree of ventilatory support provided by said delivering step to counteract a Cheyne-Stokes waxing-waning pattern of breathing as a function of said ventilatory support target measure and said input value.

12. The method of claim 11 wherein said time period is about several seconds.

13. The method of claim 12 wherein said degree of ventilatory support is dependent on a further function of said measure of respiratory airflow.

14. The method of claim 13 wherein said further function is an estimation of respiratory phase of the subject.

15. The method of claim 14 wherein said estimation of respiratory phase provides a continuous phase variable calculated from a fuzzy logic process.

16. The method of claim 15 wherein said ventilatory support target measure is about 95% of an average inspired volume and said input value is instantaneous ventilation.

17. Apparatus for the treatment of Cheyne-Stokes breathing comprising:
    means for providing a breathable gas at a controllable pressure above atmospheric to a subject;
    means for deriving a flow signal indicative of a measure of respiratory airflow of the subject; and
    a controller to operate said means for providing a breathable gas in response to said flow signal, wherein said controller comprises programmed instructions for execution by said controller, said instructions controlling the steps of:
    delivering a controlled supply of breathable gas at a pressure above atmospheric to the subject;
    calculating a ventilatory support target measure as a function of the flow signal to oppose a Cheyne-Stokes pattern of breathing;
    calculating an input value from said flow signal, said input value being derive during a time period less than that of one breath; and
    adjusting the degree of ventilatory support provided by said delivering step to counteract a Cheyne-Stokes waxing-waning pattern of breathing as a function of said ventilatory support target measure and said input value.

18. The apparatus of claim 17 wherein said time period is about several seconds.

19. The apparatus of claim 18 wherein said degree of ventilatory support is dependent on a further function of said flow signal.

20. The apparatus of claim 19 wherein said further function is an estimation of respiratory phase of the subject.

21. The apparatus of claim 20 wherein said estimation of respiratory phase provides a continuous phase variable calculated from a fuzzy logic process.

22. The apparatus of claim 21 wherein said ventilatory support target measure is about 95% of an average inspired volume and said input value is instantaneous ventilation.

* * * * *